United States Patent [19]

Makower et al.

[11] Patent Number: 5,380,290
[45] Date of Patent: Jan. 10, 1995

[54] BODY ACCESS DEVICE

[75] Inventors: Joshua Makower; Earl H. Slee; Naomi C. Chesler; William J. Gorman; Frank E. Barber, all of New York, N.Y.

[73] Assignee: Pfizer Hospital Products Group, Inc., New York, N.Y.

[21] Appl. No.: 870,140

[22] Filed: Apr. 16, 1992

[51] Int. Cl.[6] ............................................. A61M 5/178
[52] U.S. Cl. .................... 604/164; 604/160; 604/280
[58] Field of Search ............... 604/160, 164, 165, 168, 604/190, 198, 280, 158, 166, 284, 168

[56] References Cited

U.S. PATENT DOCUMENTS

| | | | |
|---|---|---|---|
| 3,734,095 | 5/1973 | Santomieri | 604/168 |
| 4,037,600 | 7/1977 | Poncy et al. | 604/160 |
| 4,099,528 | 7/1978 | Sorenson et al. | 604/164 |
| 4,417,886 | 11/1983 | Frankhouser et al. | 604/53 |
| 4,531,937 | 7/1985 | Yates | 604/53 |
| 4,747,833 | 5/1988 | Kousai et al. | 604/164 |
| 4,781,690 | 11/1988 | Ishida et al. | 604/164 |
| 4,787,892 | 11/1988 | Rosenberg | 604/164 |
| 4,798,193 | 1/1989 | Giesy et al. | 128/7 |
| 4,813,938 | 3/1989 | Raulerson | 604/167 |
| 4,887,997 | 12/1989 | Okada | 604/164 |
| 4,935,008 | 6/1990 | Lewis, Jr. | 604/164 |
| 4,983,168 | 1/1991 | Moorehead | 604/161 |
| 4,994,027 | 2/1991 | Farrell | 604/164 |
| 4,995,866 | 2/1991 | Amplatz et al. | 604/53 |
| 5,071,408 | 12/1991 | Ahmed | 606/108 |
| 5,102,394 | 4/1992 | Lasaitis et al. | 604/164 |

OTHER PUBLICATIONS

Jeffrey D. Robinson et al., "A Stepless Needle-Dilator for Expedient Percutaneous Catheterization: Technical Note", Cardiovascular and Interventional Radiology (1990) 13:329–332.

*Primary Examiner*—Randall L. Green
*Assistant Examiner*—Rob Clarke
*Attorney, Agent, or Firm*—Peter C. Richardson; Lawrence C. Akers; John L. LaPierre

[57] ABSTRACT

A device for providing access to a living body. The device, in one embodiment, includes a slotted needle dimensioned and configured to receive, in fluid tight engagement, a catheter or a guidewire introduced into the needle through the slot. The device, in another embodiment, includes a sharpened, slotted first tube, a second tube piercable by the first tube for receipt therein of at least a potion of both the first tube and the slot, and an elongated element passing into the second tube, through the slot and into the first tube. The device might further include a third tube slidably positioned around the second tube.

15 Claims, 8 Drawing Sheets

BODY ACCESS DEVICE

BACKGROUND OF THE INVENTION

The present invention pertains generally to an apparatus for providing access to a living body. More particularly, the invention relates to an improved vascular access device or introducer set used to obtain percutaneous canalization of blood vessels to facilitate the passage of catheters through tissue and vascular walls while eliminating the need to thread multiple components over a guidewire.

The purpose of an introducer set is to place a section of tubing, for example an introducer sheath for a catheter, into a vessel, or other body part, that has a sufficiently large and rigid inner diameter to facilitate insertion of other proportionately large tubes, catheters, or other instruments into said vessel or body part. An introducer set commonly contains a small diameter device with a sharp tip, commonly a hypodermic needle, so that the introduction can start with a relatively small, easily produced, puncture wound, minimizing trauma to the involved tissues. This small puncture wound is then expanded, ideally by stretching rather than tearing or cutting the involved tissues, with a tapered dilator. The wall thickness of the introducer sheath must be as small as possible, minimizing the outside diameter of the introducer sheath to minimize the trauma to the body tissues involved while maximizing the size of the inside of the opening for insertion of other devices.

One classical procedure for preparing an opening to introduce devices into a blood vessel, a body opening or other body duct is a multi-step procedure involving a number of independent devices and steps. The following steps set forth a conventional introducer set and method of use.

1) First, a hypodermic needle with glass or clear or translucent plastic syringe attached, is inserted into a vessel. When the pressure in the syringe is lower than the pressure in the vessel, blood will shoot up the needle and into the syringe where it can be observed by the operator. Observed features, such as color and rate of flow of blood, confirm that a blood vessel has been hit, and indicate the type of vessel. The ability to observe the blood is a necessary part of the procedure for blood vessel access or, for example, access to a cyst or duct.

2) Next, while holding the needle in place, the syringe is disconnected from the needle. At this point, blood can flow, or squirt, out of the proximal opening of the needle and/or air can be sucked into the needle if the pressure in the body vessel should fall below ambient pressure. This latter effect can occur in a vein during normal inspiration, when the veins often collapse under negative pressure created in the venous system by the depression of the diaphragm.

3) As quickly as possible, to minimize the above effects, a guidewire is inserted into the proximal end of the needle, effectively and approximately closing the hole and stopping fluid or air flow. The guidewire is then threaded well into the vessel. The guidewire must be flexible to turn the corner from the needle-stick track, which enters the vessel at an acute angle.

4) The needle is then removed by pulling the needle backwards over the full length of the guidewire while simultaneously holding the guidewire in place.

5) Next a dilator, with an introducer sheath slidingly positioned over it, is threaded onto the proximal end of the guidewire. The distal tip of the dilator has an inner diameter just large enough to slip over the guidewire with little friction. The outer diameter of the distal tip of the dilator is only slightly larger than the inner diameter, creating a relatively smooth transition from guidewire to dilator. The outer diameter of the dilator is tapered to a larger dimension, the taper occurring over a distance of about one or more centimeters back from the tip. The distal tip of the introducer sheath is positioned just proximal to the proximal end of the taper. As the dilator-sheath combination is pushed forwards, the tip follows the guidewire into the vessel, and the following tapered outer dimension dilates the hole through the body and the wall of the vessel, stretching the inner diameter of the vessel itself to a larger than normal diameter. The dilator must also be flexible enough to turn the corner from the needle track to the long axis of the vessel. However, a relatively large force may be required to push the dilator through all the intervening tissues and to expand the vessel diameter, so the dilator/guidewire combination must also have a proportionately large stiffness to prevent buckling. The distal end of the introducer sheath follows the dilator into the vessel. This sheath commonly has a constant inner diameter, just big enough to slip over the outer diameter of the dilator, and a constant-thickness thin wall. It must be flexible enough to pass from the body tissues outside the vessel, enter the vessel at an angle, and turn the corner to follow the long axis of the vessel. The force required again may be relatively large, but the dilator prevents buckling of the thin-walled, relatively flexible introducer sheath. Note that it would not be possible to insert the introducer sheath over the guidewire without inserting the dilator first because the required force would be great, the trauma to the tissues would be severe, and the stiffness of such a sheath would be inconsistent with the need for a flexible thin-walled device.

6) The dilator is then withdrawn, holding only the introducer sheath, and perhaps the guidewire, in place. The procedure is now complete. This introducer sheath permits repeated insertion and removal of useful devices of relatively large diameter, such as infusion catheters, balloon angioplasty catheters, angioscopes, etc. into the body and through the vessel wall without repeated trauma to vessel or intervening tissues.

The necessary threading of numerous components requires a large sterile field in which to work, is difficult to perform with just two hands, and permits blood spillage during much of the process. What is therefore needed is a system which eliminates the need for multiple threading to reduce the incidence of needle stick, the quantity of blood spillage, the time required to perform the procedure, and the sterile field required. The present invention satisfies these needs without requiring relearning of current puncture techniques. The present inventive device represents a single assembly which replaces the multiple components, each of which must be handled separately in the classical, conventional procedure. Additionally, the device of this invention can be used with ease by a single user, whereas the conventional method may generally require more than one person to handle the multiple components.

The inventive device described herein is a modified needle/catheter system whereby one inner element (i.e. a guidewire or other catheter) may be introduced into a modified needle or introducer from a position other than its proximal end in such a way that the needle or introducer may be removed for the most part non-coaxially. The device of the present invention would allow for the pre-loading of all elements prior to introduction of the assembly into the desired space or lumen (i.e. artery) and therefore reduce the time, skill and manpower necessary to thread the elements once the space has been entered. The device facilitates the introduction of catheters over a guidewire in the open surgical, laparascopic and percutaneous settings. Because the device is essentially a closed system, the risk of significant blood loss (arterial) or air-embolus (venous) during the introduction procedure is significantly reduced. The device may also allow the use of "hubbed" catheters in such situations where their use was previously prohibited (i.e. epidural anesthesia).

A preferred embodiment of this invention involves a slotted or slot-able needle, where the slot extends from a point on the body of the needle and extends towards the tip. The needle is then inserted through a tight fitting hole in the wall of a catheter and the slot oriented such that the inner lumen of the needle communicates directly with the proximal lumen of the catheter. This communication thereby allows an inner guide to be passed from the lumen of the proximal catheter to the lumen of the needle and out the needle tip. The tip of the outer catheter may be modified to fit closely to the outer aspect of the needle and may be tapered to facilitate introduction into the vessel. This outer catheter may be the primary catheter desired to be inserted into the vessel or it may be the dilator for an introducer catheter that is threaded coaxially upon its proximal end. A catheter may be generally defined as any device with a relatively flexible portion containing a lumen (i.e., a dilator, introducer catheter, or endoscope).

SUMMARY OF THE INVENTION

The present invention is directed toward a body access device comprising a needle having an outer wall and an inner diameter defining a lumen, with the wall extending between proximal and distal ends thereof and with the distal end including a sharpened tip adapted for insertion into the body; the wall further includes therein an elongated opening having a minimum width and a length communicating with the lumen and extending a predetermined distance substantially from the tip toward the proximal end; and a substantially fluid impermeable layer releasably sealing the elongated opening such that the layer does not occlude the lumen, with the layer being adapted to provide access to the opening and to the lumen. The width of the opening, in one configuration, might be less than the inner diameter of the needle, while in another version, the width of the opening might be substantially equal to the inner diameter of the needle. An elongated element, such as a guidewire, a catheter or a catheter coaxially aligned with and slidably positioned around a guidewire, might further be included for insertion through the layer and the opening and into the lumen for passage into the body. The layer might comprise at least a portion of a tubular member or sleeve, a tearable membrane, or a slit membrane. The layer might further include a port for guiding an elongated element through the layer, the opening and into the lumen. In one embodiment, the width of the opening is substantially uniform along its length, while in another embodiment, the width includes an enlarged portion along the length. In a preferred configuration, a syringe is coupled to the proximal end of the needle.

The invention further includes a body access device comprising a first tubular element having proximal and distal ends, an outer diameter, a first outer wall, a first lumen, and a sharpened tip at the distal end thereof; with the first element having an elongated opening disposed in the wall communicating with the first lumen and extending a predetermined distance substantially from the distal end toward the proximal end; and a second tubular element, such as a catheter or dilator, having proximal and distal ends, a second outer wall, and at least a second lumen, with the second lumen being dimensioned and configured to receive therein at least a portion of the first element; the sharpened tip being adapted to pass through the second outer wall at a location proximate the distal end thereof with the tip being directed toward the distal end of the second element for location of at least a portion of the elongated opening within the second lumen, a substantially fluid tight seal being created at the pass through location, with the first and second lumens being in communication. Further included might be a third tubular element, such as a catheter, having proximal and distal ends, an inner diameter defining at least a third lumen, with the inner diameter of the third lumen being greater than the maximum outer diameter of the second element and with the third element being coaxially aligned with and slidably positioned around the second element, the distal end of the third element being spaced from the pass through so that the third element is not pierced by the tip. In a preferred configuration, there is further included an elongated element, such as a guidewire, dimensioned and configured for insertion into the proximal end of the second element for sequential passage through the second lumen, the opening, and into the first lumen for passage into the body. A portion of the elongated opening not located within the second lumen is preferably sealed by a fluid impermeable layer. Preferably, at the pass through location, the wall is self-sealing and the second tubular element is bent. The outer wall of the second tubular element preferably is tapered either at the distal end thereof or at a distance from the distal end. The device might further include an aligning guide located around and coaxially aligned with the first tubular element to position the first tubular element within the second lumen.

The invention further embodies a body access device comprising a needle having proximal and distal ends, an outer diameter, an outer wall, a first lumen, a piercing tip at the distal end, and a syringe coupled to the proximal end; with the needle having an elongated opening disposed in the wall communicating with the first lumen and extending a predetermined distance substantially from the distal end toward the proximal end; and a catheter having proximal and distal ends, an inner diameter defining at least a second lumen, and a self-sealing piercable outer wall portion, with the second lumen being dimensioned and configured to receive therein at least a portion of the needle and with the piercable wall portion being located a distance from the catheter distal end substantially equal to the predetermined distance; with the distal tip of the needle piercing the catheter wall portion while maintaining a fluid tight seal, with the needle being directed toward the catheter distal end locating at least a portion of the elongated opening substantially within the second lumen, and with the first lumen and the second lumen being in communication. The device might further include a guidewire, having a diameter less than that of the first lumen, inserted into the proximal end of the catheter and passing through the second lumen to approximately the piercable wall portion location.

BRIEF DESCRIPTION OF THE DRAWINGS

FIG. 9 shows a partial plan view of a needle, much like the view of FIG. 2 but without a sleeve covering the slot, and further includes a keyhole-like opening at a location along the needle slot.

DETAILED DESCRIPTION OF THE PREFERRED EMBODIMENTS

Figures 1, 3:
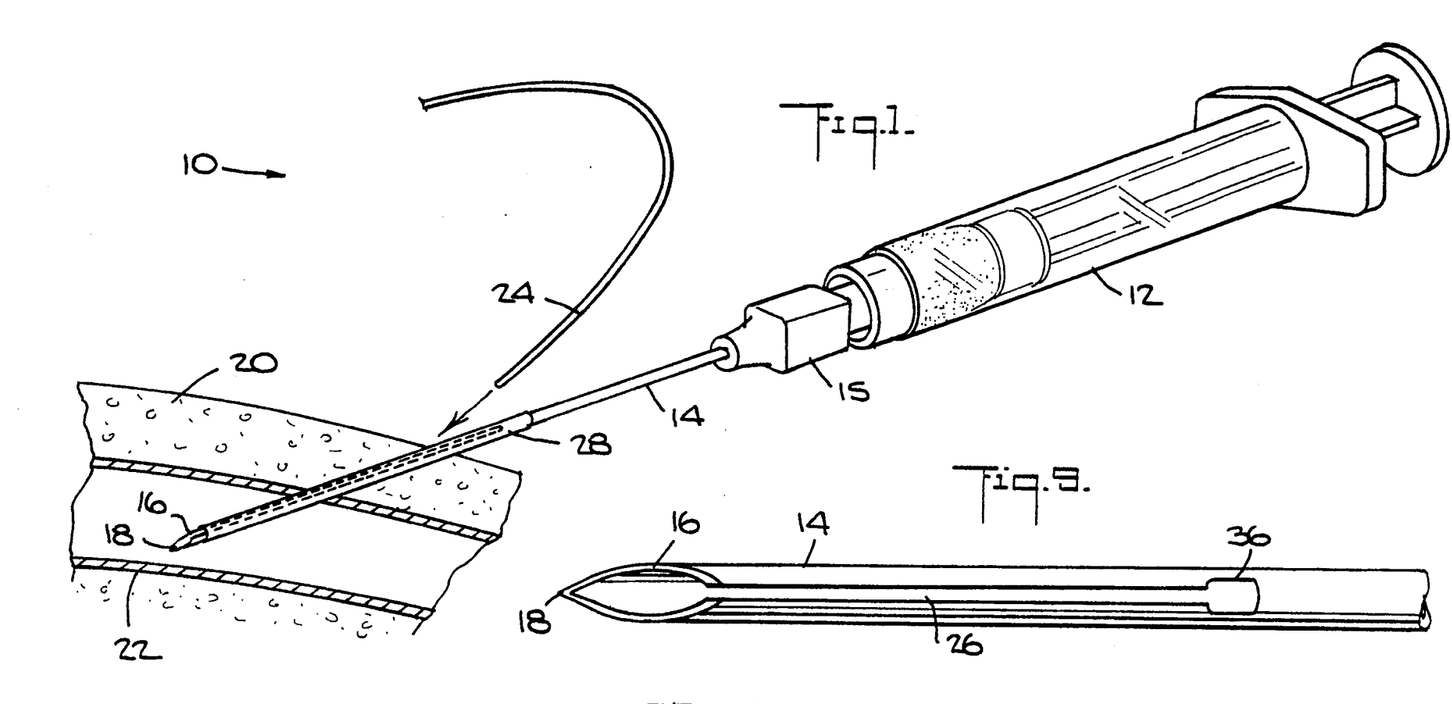
FIG. 1 is a perspective view of a first embodiment of a body access device in accordance with the principles of the present invention showing a needle, a syringe and a guidewire (about to enter the needle) with a portion of the needle being located in a blood vessel.
FIG. 3 is a partial, enlarged, sectional view of the needle and guidewire located in a blood vessel and depicting, by arrows, the path of needle entry and removal.

The description herein presented refers to the accompanying drawings in which like reference numerals refer to like parts throughout the several views. Referring to FIG. 1, in accordance with the principles of the present invention, there is illustrated a perspective view of a first embodiment of a body access device 10. Here depicted is a syringe 12 coupled to a needle 14 at proximal end or hub 15. The needle is shown with distal end 16 and sharpened tip 18 thereof being located below skin surface 20 of a living body and placed into blood vessel 22 or other body conduit. Additionally shown is an elongated element 24, such as a guidewire, dilator/catheter, positioned for entry into the needle. It should here be understood that a catheter may be generally defined as any device with a relatively flexible portion containing a lumen, that is, a dilator, introducer catheter or endoscope.

Figure 2:
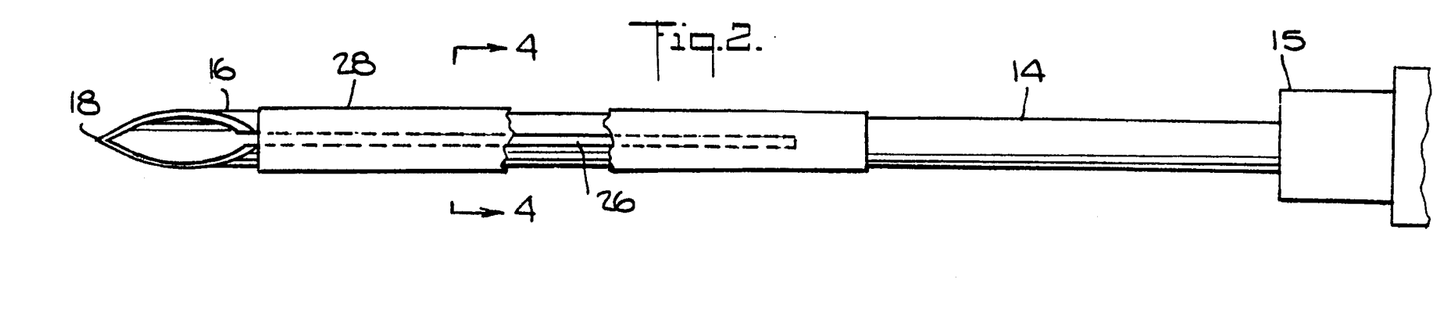
FIG. 2 is an enlarged, partial, cut-away view of the needle depicted in FIG. 1 and showing a slotted opening in the needle, with the slot being covered with a sleeve.
Figure 3:
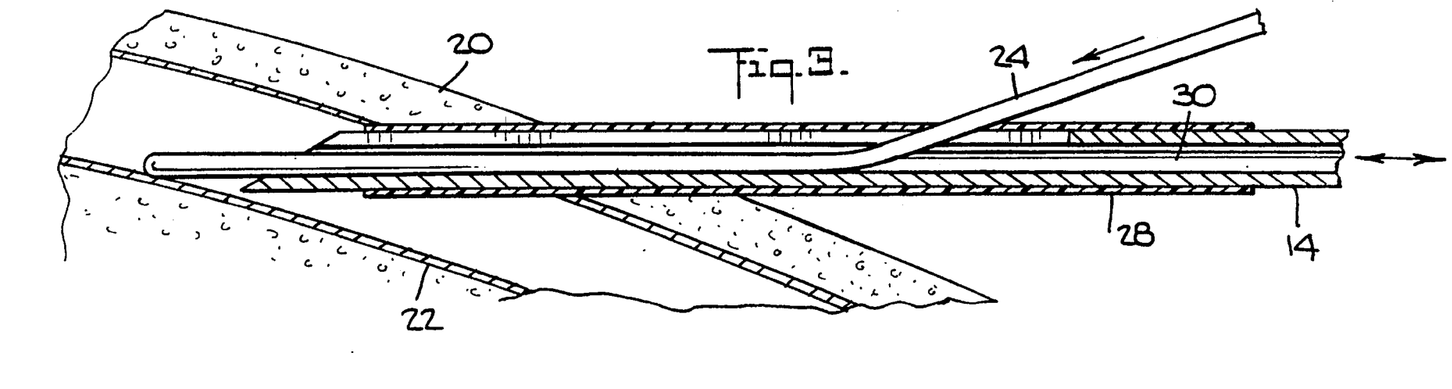
Figures 4, 5, 6, 7, 8:
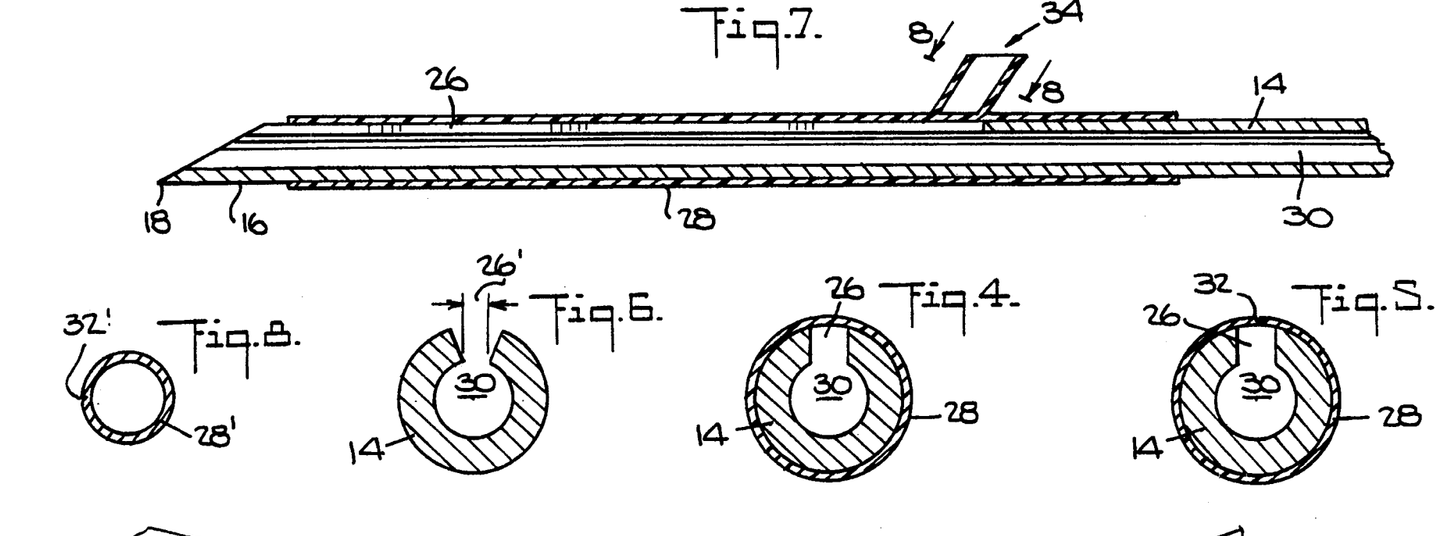
FIG. 4 is a cross-sectional view taken along line 4—4 of the needle depicted in FIG. 2.
FIG. 5 is a view like that illustrated in FIG. 4 but showing a score line in the layer over the needle slot.
FIG. 6 is a view similar to that shown in FIGS. 4 and 5 but further illustrating a needle with a modified slot configuration but without a covering over the slot.
FIG. 7 illustrates a partial sectional view of a needle and sleeve much like that depicted in FIG. 3 but further including a port for guiding a guidewire/catheter into the needle slot.
FIG. 8 is a cross-sectional view taken along line 8—8 of the guide port depicted in FIG. 7.
Figures 10, 12:
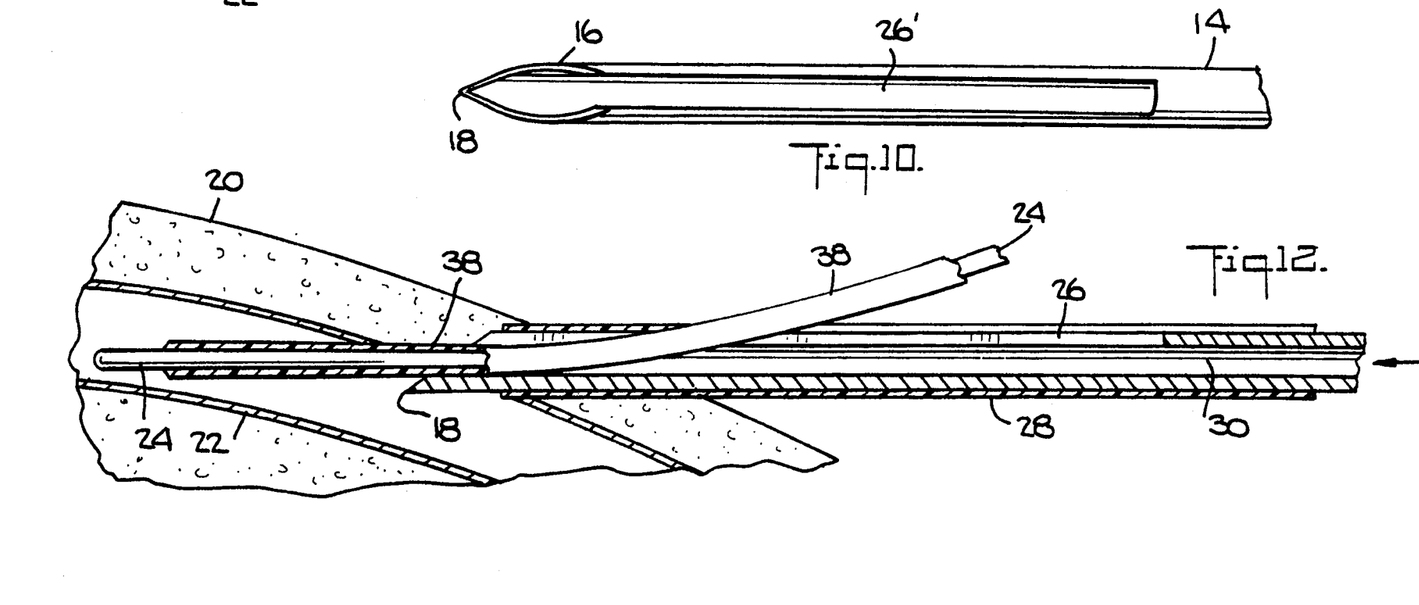
FIG. 10 illustrates a needle and slot, without a sleeve covering the slot, but with the slot enlarged to also accommodate a larger element such as a catheter in addition to or in place of a guidewire.
FIG. 12 is substantially the view of FIG. 11 but in partial section and showing further advancement of the catheter/dilator into the vessel, the needle being partially withdrawn, and arrows indicating the pathway for needle advancement and withdrawal.

An enlarged, partial, cut-away view of the needle of FIG. 1 is shown illustrated in greater detail in FIG. 2. Here it is illustrated that needle 14 has a slotted opening 26 along the needle length and a fluid impermeable layer 28 covering a substantial portion of the slotted opening. Layer 28 is shown as a tubular member or a sleeve and the layer may comprise a tearable membrane or a slit membrane. The tearable membrane could be scored, perforated or thinned at least along that portion covering the slot. The layer may be piercable by a guidewire or catheter and may include a port (FIG. 7). FIG. 3 shows that element 24 has passed through layer 28, entered lumen 30 of needle 14, and has advanced into blood vessel 22. The arrows to the right in FIG. 3 indicate the pathway traveled by element 24 and needle 14. Customarily, the needle will be rotated through an angle of approximately 180° before it is removed from the body. FIG. 4, taken along sight line 4—4 of FIG. 2, illustrates needle 14 covered by layer 28 (in this version a tearable member) and further depicts opening 26 and needle lumen 30. The opening 26 is shown to be smaller than the inner diameter or lumen of needle 14. However, although not shown, the opening may be substantially equal to the needle lumen. FIG. 5 is a view similar to that of FIG. 4 but depicts layer 28 as being slit or scored at notch 32. Notch 32 might run substantially the full length of layer 28 but at least it should run the length of the layer over the elongated opening or slot in the needle. FIG. 6 again shows needle 14 in section but without slot covering layer 28. It should be understood, however, that the slot would be covered. This view is meant to show that the opening has a minimum width 26'. FIG. 7 illustrates a view of needle 14 like that shown in FIG. 3 but without element 24 and further includes a port 34 for guiding a guidewire/catheter into opening or slot 26. FIG. 8 shows the port in cross section. Generally, the port is constructed of material 28', which is generally the same material as layer 28, and it may be integral with or attached to layer 28. Additionally, the port might include notch 32' which possesses the same features as notch 32 shown in FIG. 5 and discussed above. A fluid-tight piercable seal is disposed at the juncture of the port and needle slot. FIG. 9 illustrates many of the features herein described in respect to needle 14 but without layer 28 covering the needle slot 26 and further includes a keyhole-like opening 36 along slot 26. Opening 36 is an enlargement of the width of opening 26 which heretofore has been illustrated and described as being substantially uniform along its length. Enlarged opening 36 can accommodate a guidewire (not shown) which includes a reduced portion along its length that is slightly less than the minimum slot width. This will allow for the insertion of a guidewire having a necked-down portion with a diameter or dimension less than the needle slot minimum width but a diameter or dimension greater than the slot width along any remaining portion of the wire. However, it should be understood that the guidewire diameter or dimension cannot exceed the diameter of needle lumen 30 through which the guidewire passes and, in fact, it should be slightly less than the lumen diameter. FIG. 10 depicts needle 14 having an enlarged opening or slot 26' for the accommodation of a larger element such as a catheter.

Figure 11:
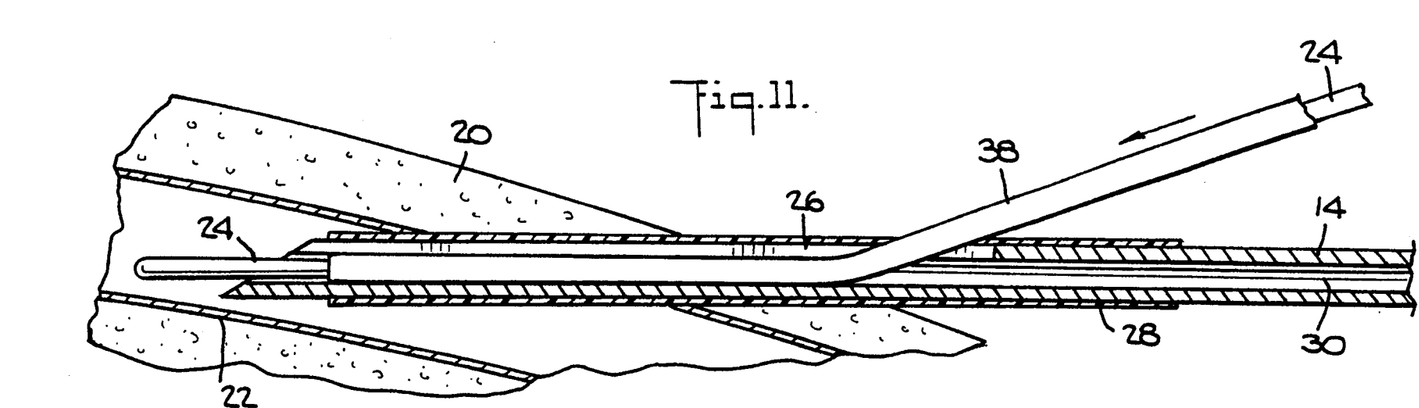
FIG. 11 is a view much like that depicted in FIG. 3 but additionally showing a catheter/dilator advanced over the guidewire and into the vessel.

Turning next to FIGS. 11 and 12, there are shown views much like that depicted in FIG. 3. In FIG. 11, a catheter/dilator 38 is shown being advanced over guidewire 24, through layer 28 and opening 26 and into and along lumen 30 of needle 14. Typically, the needle of FIG. 10 with enlarged opening 26' might be used for this procedure. The needle has previously been inserted into blood vessel 22. The arrow indicates the direction of catheter/dilator advancement. In FIG. 12, there is shown further advancement of the combined guidewire and catheter/dilator into blood vessel 22 and partial withdrawal of needle 30. The arrows indicate the general direction of needle entry and withdrawal from the blood vessel. As aforesaid, the needle is generally rotated through a 180° turn before removal from the vessel.

Figures 13, 15:
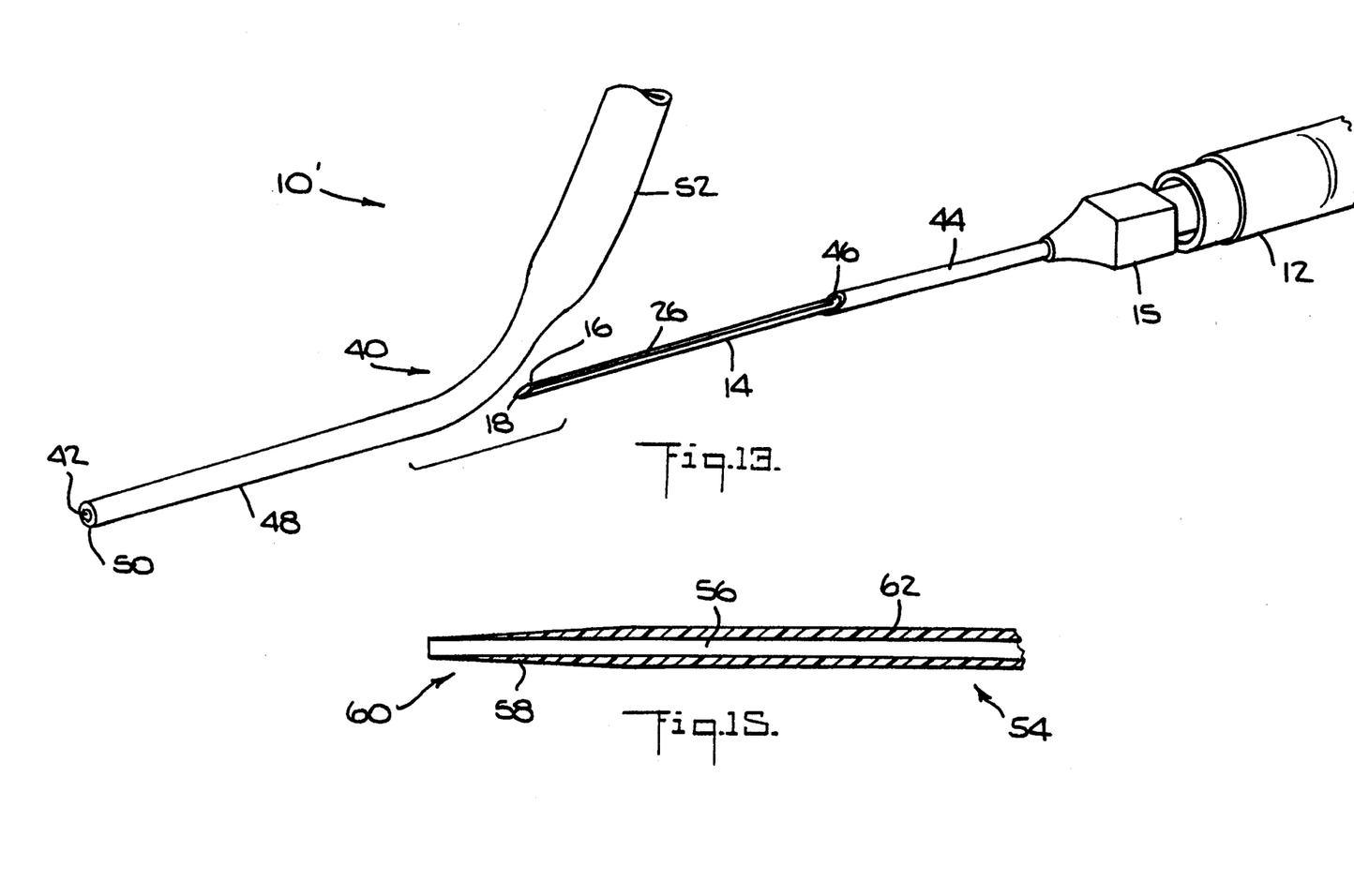
FIG. 13 is a perspective view of a second embodiment of a body access device in accordance with the principles of the present invention showing a slotted needle, a syringe and a dilator, with the needle being positioned to next pierce the outer wall of the dilator for location of a portion of the needle in the dilator lumen.
FIG. 15 is a sectional view of the end of the dilator of FIG. 14 showing a gradual outer wall taper from the distal toward the proximal end of the dilator.
Figures 14, 16, 17:
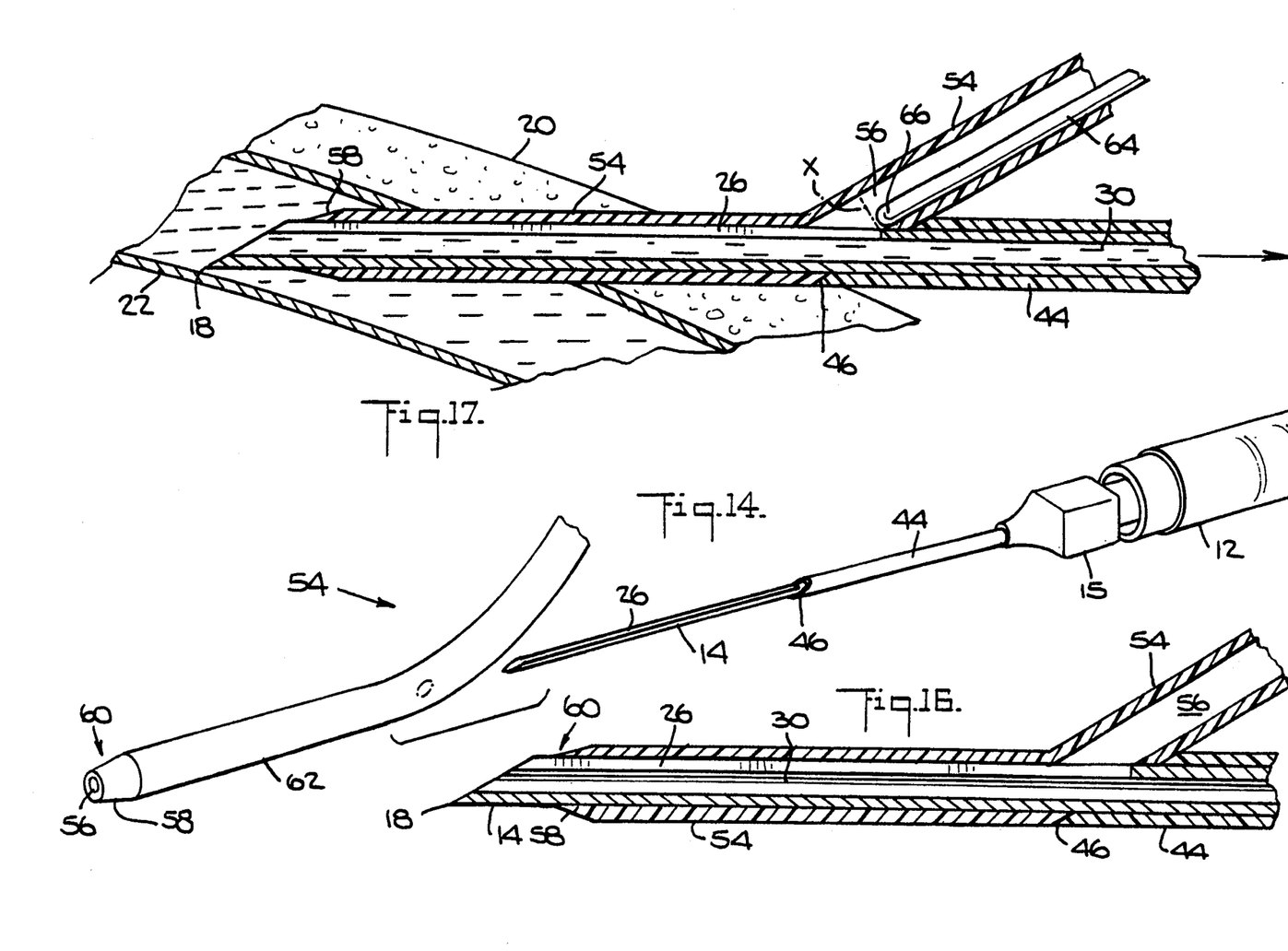
FIG. 14 is a view like that depicted in FIG. 13 but showing a tapered portion of the outer wall of the dilator at the distal end and a uniform outer wall diameter thereafter towards the dilator proximal end.
FIG. 16 is an enlarged, sectional view of the needle and dilator of FIG. 14 and illustrates the location of the needle in the dilator lumen.
FIG. 17 is a view like that depicted in FIG. 16 but additionally showing the needle and dilator located in a blood vessel, a guidewire about to enter the needle slot, and the path (arrow) the needle is to follow upon needle removal after advancement of the guidewire into the needle slot and into the blood vessel.

Turning now to FIG. 13, in accordance with the principles of the present invention, there is illustrated a perspective view of another embodiment of the body access device herein designated 10'. Here depicted is syringe 12 coupled to needle 14 (with opening 26) at proximal end or hub 15. The needle has a sharpened tip 18 at distal end 16. The needle is positioned to pierce the outer wall of dilator 40 for location of a portion of the needle in lumen 42 of dilator 40. In one preferred configuration needle 14 will include needle stop 44 to control the advancement of the needle into dilator 40 and beveled end 46 of the needle stop to assure appropriate orientation of the needle within the dilator as will later be discussed. Dilator 40 might include an outer wall portion 48 of substantially constant diameter extending from distal end 50 a selected distance before tapering to an outer wall portion 52 of increased diameter. FIG. 14 is a view like that depicted in FIG. 13 but shows a dilator 54 having a lumen 56 and tapered portion 58 at the distal end 60 and an outer wall 62 of substantially uniform diameter towards the proximed end (not shown). FIG. 15 is a sectional view of the distal end 60 of dilator 54 showing the gradual taper 58 of the outer wall from the distal toward the proximal end. Preferably, end 60 is just slightly greater in diameter than the diameter of the needle near the needle distal end. The slightly increased diameter and taper provide for ease of entry of the dilator and needle into a body vessel. It should be understood that dilator 40, 54 could be replaced by a catheter.

Figures 18, 19:
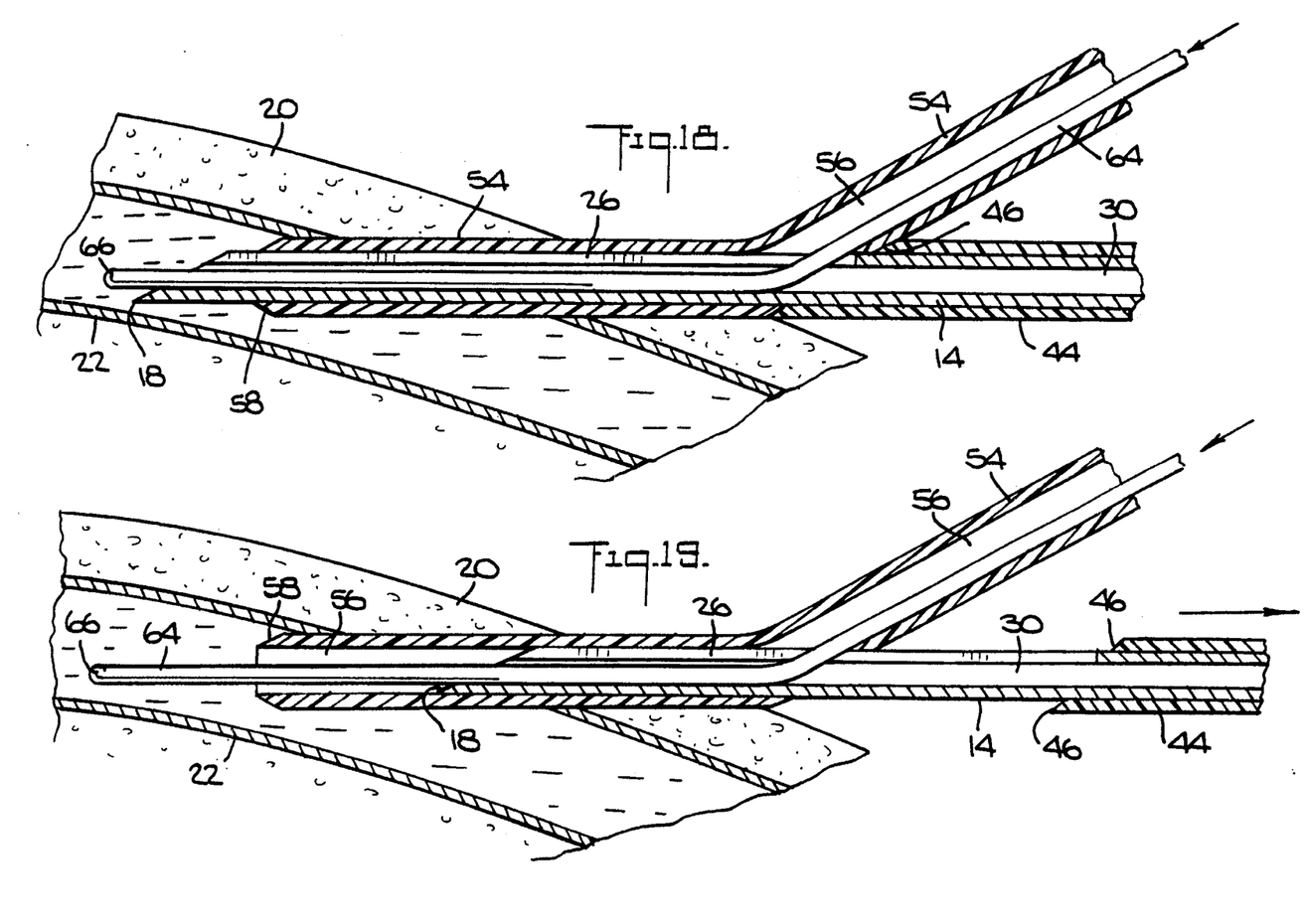
FIG. 18 is substantially the view of FIG. 17 but additionally illustrates placement of the guidewire in the blood vessel and prior to needle withdrawal.
FIG. 19 depicts a view much like that of FIG. 18 showing further advancement of the guidewire into the blood vessel and partial removal of the needle.
Figures 20, 21:
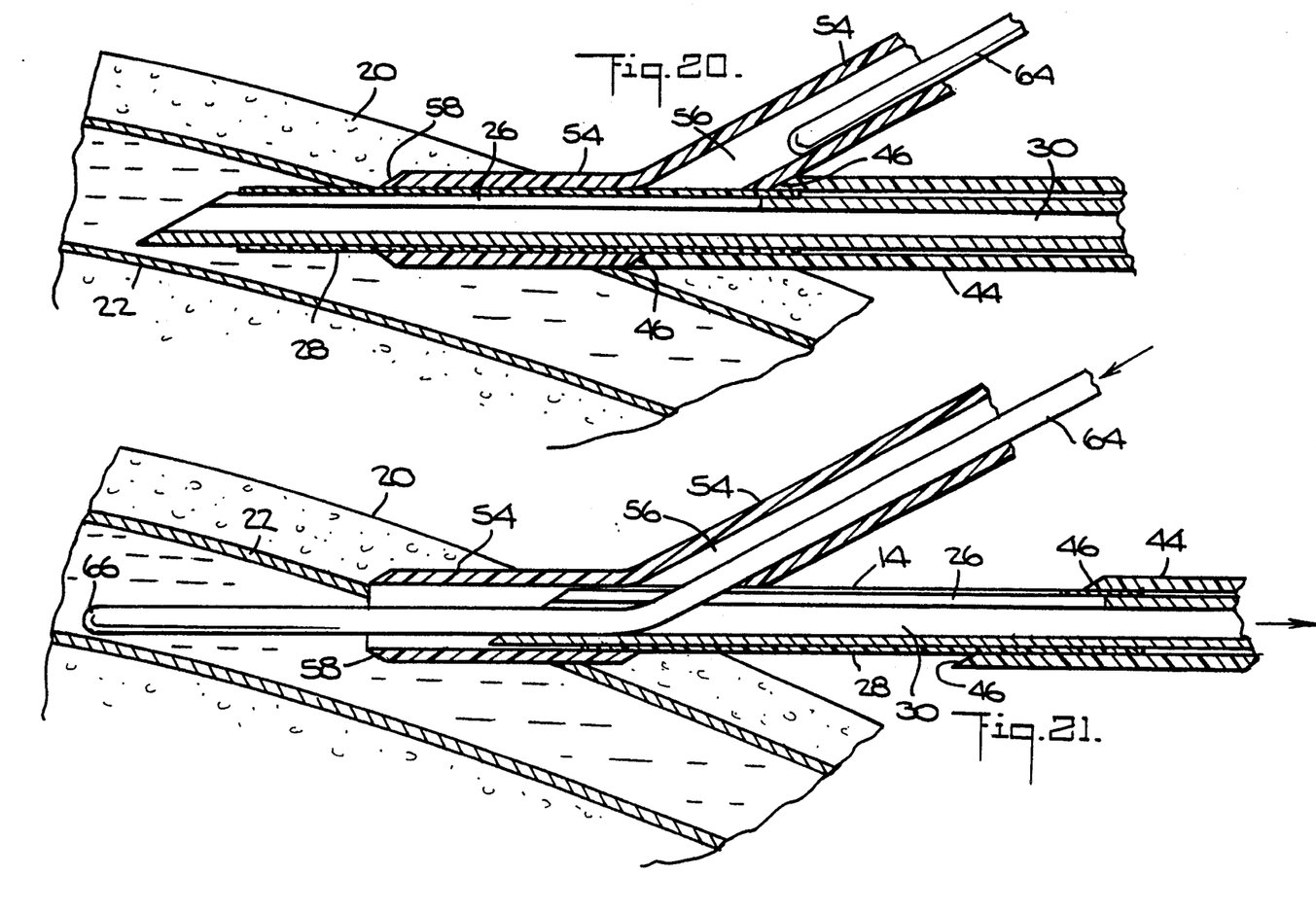
FIG. 20 this view is one much like that shown in FIG. 17 but additionally includes a membrane covering the needle slot.
FIG. 21 depicts a view like that of FIG. 20 but further illustrates advancement of the guidewire into the blood vessel and partial removal of the needle.

Turning next to FIGS. 16–20, there is therein illustrated the body access device of FIG. 14 prepared for use (FIG. 16) and in use in a living body (FIGS. 17–19 and 20). In FIG. 16, needle 14 has pierced the wall of dilator 54 and is shown positioned within dilator lumen 56. Needle stop 44 with beveled end 46 has positioned the needle within the dilator such that opening 26 is in, or adapted to be placed in, communication with dilator lumen 56 at or near the needle pass through location for immediate or subsequent communication with the proximal end of the dilator. A substantially fluid-tight seal exists at the needle pass through location along the plane of level 46. The outer wall of the dilator at the needle entry location is self-sealing, with the outer wall preferably being made of an elastomeric material. Alternatively, a valve, slit valve or the like, might be used. FIG. 17 is a view substantially like the view of FIG. 16 but additionally shows needle 14 and dilator 54 positioned within vessel 22. Additionally, a guidewire 64 with distal end 66, located within lumen 56 of dilator 54, is about to enter needle slot 26. Although not shown in this view, an air seal could be located at or near the interface (in phantom) between lumen 56 and opening 26 just below the tip of the guidewire. This would guard against undesirable entry of air into slot 26 from lumen 56 through that portion wherein the guidewire 64 is located. Alternatively, an air tight seal (not shown) could be included at the proximal end of dilator 54. Another approach (not shown) might be a reduction of the inner diameter of the dilator 54 near distal end 66 of guidewire 64 generally at location x shown in FIG. 17. Still yet, a saline solution might be included in the dilator lumen from approximately location x toward the proximal end of the dilator, that is, the end opposite distal end 60. Any of these approaches could be employed to reduce the incidence of air introduction into the needle opening and needle lumen. The arrow to the right in FIG. 17 shows the direction the needle will follow upon subsequent needle removal from the vessel and body. FIG. 18 shows advancement of guidewire 64 into opening 26, lumen 30 and into blood vessel 22. In this view, needle 14 is positioned as shown in FIG. 17. In FIG. 19 there is shown further advancement of guidewire 64 into blood vessel 22 and partial withdrawal of needle 14. As stated previously, in practice the needle will probably be rotated approximately 180° before withdrawal. Lastly, FIG. 20 is a view like that of FIG. 17 but additionally includes a piercable fluid impermeable layer 28, like that earlier discussed, substantially covering opening 26 to insure that the opening is sealed, particularly where the opening might not be fully positioned within lumen 56 of dilator 54. This is to guard against the unwanted introduction of air or loss of blood.

Figure 22:
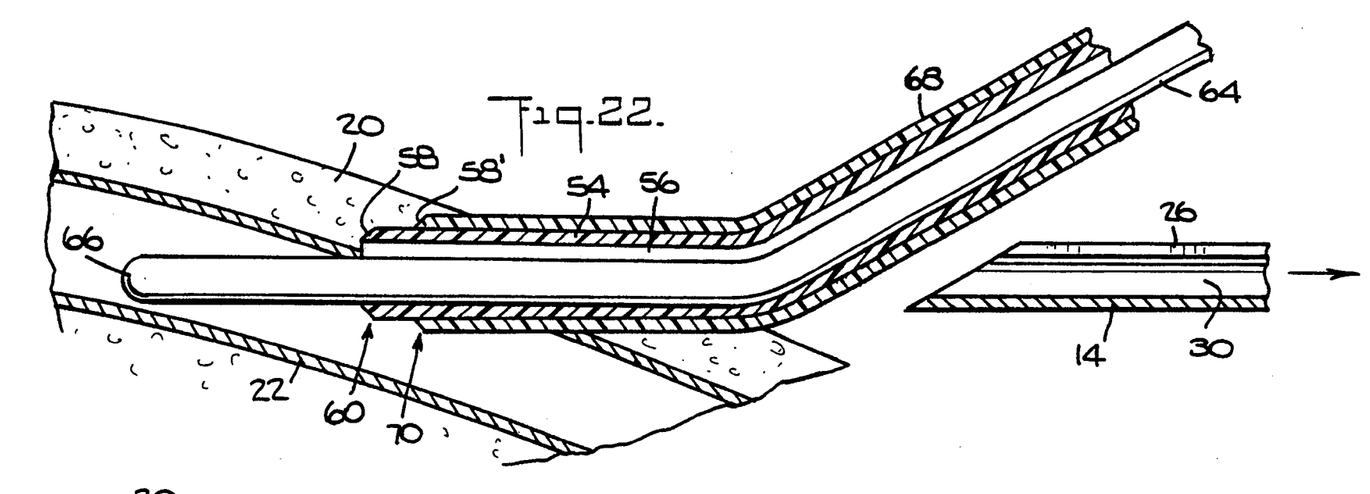
FIG. 22 is a view like that of FIG. 21 but further depicts a catheter advanced over the dilator and removal of the needle.
Figure 23:
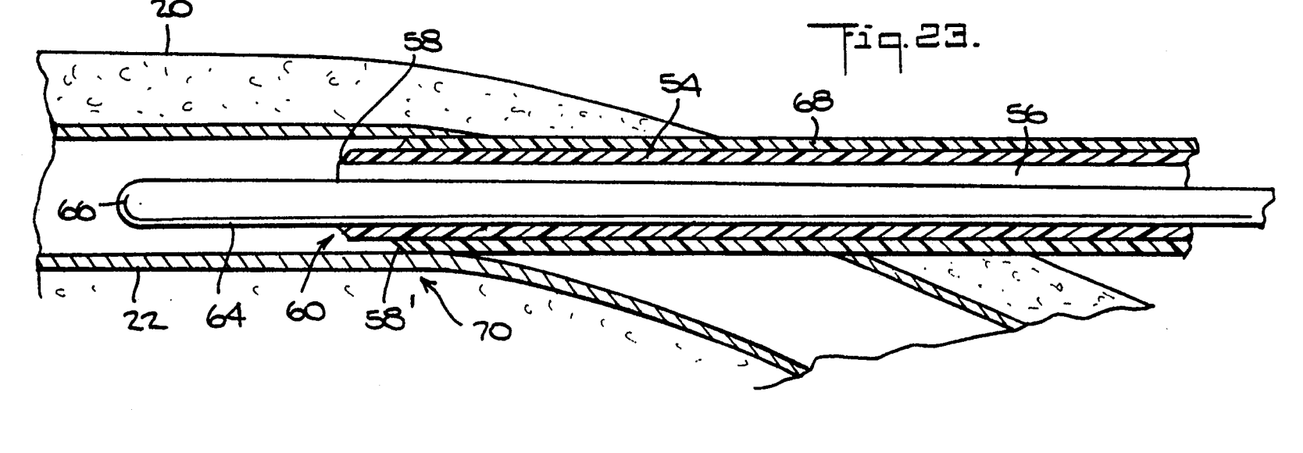
FIG. 23 illustrates placement of the guidewire, dilator and catheter of FIG. 22 in the blood vessel.

Turning now to FIGS. 21-23, FIG. 21 depicts a view much like that of FIG. 20 but shows that guidewire 64 has advanced into blood vessel 22 and that needle 14 has been withdrawn from vessel 22 and partially withdrawn from the body. Again, partial needle revolution prior to withdrawal has not been illustrated but in all probability it will take place in practice. FIG. 22 illustrates a view much like that of FIG. 21 but further depicts a catheter or sheath 68, having a tapered portion 58' (much like that of 58) at distal end 70, slidably advanced over dilator 54 and removal of needle 14. FIG. 23 illustrates the straightening of the dilator and catheter of FIG. 22 and the placement of dilator 54, guidewire 64, and catheter 68 in blood vessel 22.

In a preferred form of the invention, a hypodermic needle has a longitudinal slot in it, starting at the most proximal location on the distal opening of the needle. The opening is normally an oval-shaped bevel at an acute angle relative to the long axis of the needle, creating a sharp point at the most distal end of the opening and an oval-shaped curvature at the most proximal location on the opening. The slot extends back along the needle a distance that must be somewhat longer than the distance from the skin, or the outside of the body being entered, to the near-wall of the vessel or opening to be cannulated. The transverse width of the slot must be at least somewhat larger than the diameter, or a neck down segment, of a guidewire allowing the guidewire to freely slide into and out of the slot in a direction non-coaxial with the long axis of the needle. The needle may be smaller in diameter than that used for a conventional device, such that the guidewire, generally small enough to slide coaxially within the needle, may also be smaller than in the conventional device. A needle-stop may be attached to the needle at the proximal end of the slot and the modified needle connected to a syringe in the conventional manner. A modified dilator, having an inner diameter at its tip just large enough to slip over the outside of the slotted portion of the needle and having a thin wall at the tip, is provided. The dilator may be tapered over a 1-3 cm. length to a larger outer diameter towards the proximal end. A small slit is made in the sidewall of the dilator at a certain distance from the distal tip of the dilator, the distance being approximately equal to the length of the slot in the needle.

The components may be preassembled. The needle-stop is placed on and secured to the needle. In a preferred embodiment the needle-stop consists of the distal end of a stop-sheath placed, and fitting slidingly but snugly, over the needle. The distal end of said stop-sheath is beveled. The precise angle and location of the bevel and its purpose are described below. The syringe is attached to the needle, as in the conventional method. The distal end of the dilator is inserted into the proximal end of the catheter or introducer sheath, and advanced so that the part of the dilator with the small slit can be seen protruding beyond the distal end of the introducer sheath. Alternatively, the slit in the dilator can be created by the tip of the needle in a later step. In this case, the location of the slit must be pre-marked on the dilator and the introducer sheath is advanced a measured distance, equivalent to that described above.

The tip of the needle is then inserted into the slit in the wall of the dilator, or equivalently the needle is inserted into the marked location on the dilator, creating the slit by its insertion. The rotational position of the needle, relative to the dilator is set and maintained so that the slot of the needle is aligned with the slit of the dilator. As the needle is inserted into the dilator, an acute angle is maintained between the needle and the dilator, such that the sharpened tip of the needle can advance towards the distal end of the dilator. The needle is advanced until the sharp tip of the needle just protrudes from the tip of the dilator. At that point the slit in the dilator should be abutting against the stop on the needle, forming an effectively sealed, "Y"-shaped lumen, with the common leg of the "Y" being the slotted lumen of the needle, and the branches of the "Y" being the un-slotted, more proximal, portion of the needle, and the lumen of the dilator proximal to the slit. The acute angle between the needle and the dilator is defined by the acute angle of the beveled end of the needle-stop.

The guidewire is then inserted into the proximal end of the dilator and advanced a fixed distance such that the distal tip of the guidewire is adjacent to, but does not interfere with, the lumen of the slotted needle. The tip of the guidewire effectively and temporarily closes off the dilator branch of the "Y"-shaped lumen, leaving the lumen from the needle tip opening to the syringe completely open, as required for withdrawal and observation of blood or fluid during insertion. The guidewire can be fixed in place by a temporary guidewire-stop abutting the proximal end of the dilator to prevent the tip of the guidewire from occluding the needle/syringe lumen. The unitary assembly can then be packaged and sterilized for use in the sterilized field in the operating arena.

In use the sharp tip of the needle/dilator is inserted so that the tip of the needle and the tip of the dilator are simultaneously in the vessel. If appropriate, the needle/dilator should be rotated about the long axis so that the sharp tip of the needle is furthest away from the far wall of the vessel. This is done since the tip of the dilator in the invention device may be somewhat proximal, by a fraction of a mm only, from the needle opening compared with the conventional device in which the dilator is not part of the needle-stick part of the procedure. The described rotation reduces the risk of perforating the far wall of the vessel with the sharp tip of the needle. Since the needle/syringe lumen is relatively unchanged from the conventional device, blood flowing into the syringe can be observed to verify the type and size of the blood vessel, as is required.

Next the guidewire-stop is removed and discarded and the guidewire is advanced through the needle/dilator and then some distance into the vessel. One advantage of the invention is that this step does not require removal of the syringe and the insertion of the tip of the guidewire into the proximal opening of the needle while blood is flowing out or, possibly, while air is flowing in.

Next, holding the externally exposed part of the dilator in the fingers of one hand and the needle/syringe in the other, the needle is withdrawn by sliding it out of the inside of the dilator, the dilator being initially held in place to prevent its being withdrawn from the blood vessel. The needle and syringe can be discarded. The dilator is then advanced along the guidewire to complete the dilation part of the procedure. If the guidewire is sufficiently longer than the dilator, the dilator can be advanced simultaneously with the guidewire, or the guidewire and the dilator can be advanced separately.

Once the dilator is in place, the guidewire can be removed if desired. The introducer sheath is then advanced with the dilator into position. Finally the dilator is removed leaving the introducer sheath in place, and the introducer method is complete.

The body access device of the present invention has a number of potential uses. Such uses might include, but not be limited to, (1) central venous access for insertion of catheters into the central venous system; (2) angiography, both coronary and peripheral, for injection of dye into veins or arteries; (3) angioplasty, both coronary and peripheral, for access to vessels and for the insertion of baloon catheters into vessels; intralumenal atherectomy/thrombectomy, both arterial and venous; (4) laparoscopic procedures: cholecystectomy to allow for access to the gall bladder and cystic duct; catheterization of internal organs, vasculature and ducts (e.g., the portal vein, the portal artery and the liver, the mesenteric vein and the colon, the kidney, and the pancreatic duct); introduction of shunts; (5) access to the lung during thoracentesis to lessen probability of pneumothorax; (6) optical catheters to reduce the risk of air emboli during eye catheterization; and (7) epidural catheterization to allow the use of hubbed catheters.

We claim:

1. A body access device comprising a first tubular element having proximal and distal ends, an outer diameter, a first outer wall, a first lumen, and a sharpened tip at said distal end; said first element having an elongated opening longitudinally disposed in said wall communicating with said first lumen and extending a predetermined distance substantially from said distal end toward said proximal end; said opening being dimensioned and configured and adapted to receive therein an elongated element; a second tubular element having proximal and distal ends, a maximum outer diameter, a second outer wall, and at least a second lumen, with said second lumen being dimensioned and configured to receive therein at least a portion of said first element; said sharpened tip being adapted to pass through said second outer wall at a location proximate said distal end thereof, with said tip being directed toward said distal end of said second element for location of at least a portion of said elongated opening within said second lumen, a substantially fluid tight seal being created at said pass through location, with said first lumen and said second lumen being in communication, wherein said elongated element may be introduced into and removed from said opening substantially non-longitudinally; and a third tubular element having proximal and distal ends, an inner diameter defining at least a third lumen, with said inner diameter of said third lumen being greater than the maximum outer diameter of said second element and with said third element being coaxially aligned with and slidably positioned around said second element.

2. A body access device comprising a first tubular element having proximal and distal ends, an outer diameter, a first outer wall, a first lumen, and a sharpened tip at said distal end; said first element having an elongated opening longitudinally disposed in said wall communicating with said first lumen and extending a predetermined distance substantially from said distal end toward said proximal end; said opening being dimensioned and configured and adapted to receive therein an elongated element; a second tubular element having proximal and distal ends, a maximum outer diameter, a second outer wall, and at least a second lumen, with said second lumen being dimensioned and configured to receive therein at least a portion of said first element; said sharpened tip being adapted to pass through said second outer wall at a location proximate said distal end thereof, with said tip being directed toward said distal end of said second element for location of at least a portion of said elongated opening within said second lumen, a substantially fluid tight seal being created at said pass through location, with said first lumen and said second lumen being in communication, wherein said elongated element may be introduced into and removed from said opening substantially non-longitudinally; and a third tubular element having proximal and distal ends, an inner diameter defining at least a third lumen, with said inner diameter of said third lumen being greater than the maximum outer diameter of said second element and with said third element being coaxially aligned with and slidably positioned around said second element, said distal end of said third element being spaced from said pass through so that said third element is not pierced by said tip.

3. The device according to claim 2 further including an elongated element being dimensioned and configured and adapted for insertion into said proximal end of said second element for passage sequentially through said second lumen, said opening and into said first lumen for passage into said body.

4. The device according to claim 2 wherein a remaining portion of said elongated opening not located within said second lumen is sealed by a fluid impermeable layer.

5. The device according to claim 2 wherein said second element is a dilator.

6. The device according to claim 2 wherein said third element is a catheter.

7. The device according to claim 2 wherein said elongated element is a guidewire.

8. The device according to claim 2 further including a syringe coupled to said proximal end of said first element.

9. The device according to claim 2 wherein said second outer wall at said pass through location is self-sealing.

10. The device according to claim 2 wherein said second outer wall tapers from a first minimum diameter at said distal end thereof to said maximum outer diameter.

11. The device according to claim 2 further comprising an aligning guide being disposed around and coaxially aligned with said first tubular element to position said first tubular element within said second lumen.

12. The device according to claim 2 wherein said second tubular element is bent at said pass through location.

13. The device according to claim 2 wherein said second outer wall has a first minimum substantially constant diameter disposed from said distal end thereof and extending a predetermined distance along said second tubular element and thereafter said second outer wall tapers to said maximum diameter.

14. The device according to claim 13 wherein said minimum diameter is slightly greater than the outer diameter of said first tubular element.

15. The device according to claim 2 further including an air seal disposed in said at least a second lumen.

* * * * *